United States Patent [19]

Garabedian

[11] Patent Number: Plant 5,908

[45] Date of Patent: Mar. 17, 1987

[54] GRAPEVINE, "FOUR FIVE"

[76] Inventor: John M. Garabedian, 3104 E. Huntington Blvd., Fresno, Calif. 93702

[21] Appl. No.: 766,445

[22] Filed: Aug. 19, 1985

[51] Int. Cl.[4] ..... A01H 5/03

[52] U.S. Cl. ..... Plt./47

[58] Field of Search ..... Plt./47

*Primary Examiner*—Robert E. Bagwill

*Attorney, Agent, or Firm*—Worrel & Worrel

[57] ABSTRACT

A grapevine generally resembling the Delight variety of grape (unpatented), but distinguished therefrom by bearing berries which ripen at least two weeks earlier than the Delight variety, and which is substantially free from the distinct muscat flavor characteristic of the Delight variety.

1 Drawing Figure

BACKGROUND OF THE NEW VARIETY

The present invention relates to a new and distinct variety of grapevine to be known as the "Four Five" and more particularly to such a grapevine bearing white, almost seedless berries characterized as to novelty by a date of ripening at least two weeks earlier than the Delight variety, which it most nearly resembles.

From a commercial standpoint, the relative times of ripening of various varieties of grapes is obviously extremely important. It has been recognized as desirable to provide grapevines that bear fruit earlier than the varieties which it most nearly resembles, whereby the fruit can be brought to market at a time when competition is at a minimum. In addition, if the ripening periods of various grapes can be spread over a longer period of time, savings and increased efficiency can be attained because the capital outlay which is generally required to harvest and then transport these grapes which are harvested within a relatively short ripening period can be spread over a longer period of time resulting in lower cost of the final product and increasing the uniformity of production.

The new and distinct subject variety of grapevine, hereinafter referred to as the "New Variety", most closely resembles the variety "Delight", but matures at least two weeks earlier. In addition, the New Variety does not have the light muscat flavor of the Delight variety.

ORIGIN AND ASEXUAL REPRODUCTION OF THE NEW VARIETY

The New Variety was originated and discovered by me in 1968 at my farm located at 5841 East Kings Canyon Road, near the City of Fresno, in the County of Fresno, in the State of California.

The New Variety was selected from a multiplicity of seedlings resulting from cross-pollination under my supervision and control by an Almeria variety vine (female) and an unknown male parent. The New Variety was asexually reproduced in 1977, also under my supervision and control, by Dr. Sayed A. Badr of Fresno, Calif., employed by me for the purpose, by soft wood cuttings that were made from the original grapevine of the New Variety which was located at the designated farm. The grape and vine characteristics resulting from the soft wood cuttings have continuously been observed by me and have proved to be identical to those of the original vine.

SUMMARY OF THE NEW VARIETY

The New Variety of grapevine is generally characterized by its bearing a Light-Green, oval-shaped, substantially seedless berry that resembles in some characteristics the variety "Delight" but which matures at least two weeks earlier than the Delight. The New Variety bears fruit which ripens for commercial harvesting between June 25 and July 5 in the Fresno area.

BRIEF DESCRIPTION OF THE DRAWING

The accompanying drawing is a color photograph displaying two bunches of mature grapes of the New Variety together with the representative leaves of such variety.

DETAILED DESCRIPTION

Referring more particularly to the pomological details of this new and distinct variety of grapevine, the following has been observed under the ecological conditions prevailing at the designated farm. The color code identifications are by reference to the Munsell Limit Color Cascade. Common descriptive color names are also used.

VINE

Generally: Upright and open in configuration as controlled by pruning techniques; medium in size; growth, medium to vigorous; hardy; productive, a typical young vine produces one or two large clusters per shoot.

Trunk: Medium in size; bark is loose and shreddy in texture.

Canes: Numerous and straight.

*Thickness.*—Medium.

*Length.*—Average length, 5 to 5.5 feet (1.52 to 1.6 meters).

*Color.*—Yellow to Yellowish-Green, Brown color when mature (MCC 23-8 to 24-9).

*Nodes.*—Enlarged.

*Internodes.*—Medium to long, ranging from 3.5 to 6.5 inches, (8.89 cm. to 16.51 cm.).

*Tendrils.*—Long; smooth and thick; intermittent or discontinuous; equally bifurcated and trifurcated.

Flowers: Fertile; upright and well developed stamens which range in length from 5 to 9 mm. in length; early blooming in respect to other varieties.

*Earliest first bloom.*—May 17; latest first bloom May 25; stamens produce good amounts of pollen; flower clusters are produced on the third through fifth node, as the nodes are numbered from the base of the shoot.

Leaves:

*Texture.*—Glabrous.

*Size.*—Medium to large; thickness — thin.

*Form.*—Roundish; 3 to 5 lobes, with the terminal lobe being acuminate; Petiolar sinus of medium depth and occasionally overlapping; basal sinus and each lateral sinus deep in depth, although this sinus may sometimes be shallow or very shallow in exposed leaves; medium in width.

*Margin.*—Pinnatifid with teeth of narrow width and shallow depth.

*Color.*—Upper Surface — Dark Green (MCC 18-14); Lower Surface Color — Pale Green (MCC 16-6).

FRUIT

Maturity: Early-season, June 25 through July 5 in 1981.

Form: Variable, being mostly oval and elongated; having medium adherent shells.

Size: Mostly medium.

Skin: Thin and tender; skin adheres to the pulp.

*Color.*—White, which turns to an amber color when overripe; the grape has a thin bloom.

Flesh: Translucent and white; soft, juicy and sweet.

Seeds: Vestigal only; small, short and narrow; varying from 2 to 4 per berry, and not noticeable when eating.

Cluster: Large and long, ranging in length from 10 to 15 inches (25.4 cm. to 38 cm.); cylindrical in appearance; medium in density; regular and double shouldered.

Peduncle:

*Length.*—Short; approximately ¾ to 1 inch long (1.9 cm. to 2.45 cm.).

*Thickness.*—Medium thick.

Pedicel:

*Length.*—Medium.

*Thickness.*—Slender, with no or very few warts.

Keeping quality: Fair.

Shipping quality: Fair.

Freedom from shatter: May shatter.

Eating quality: Very good, with a soft, juicy and sweet flesh.

Uses: Primarily for market use, but also suitable for resin production.

Although the new variety of grapevine possesses the stated characteristics under the growing conditions prevailing in Fresno County, Calif., in the central part of the San Joaquin Valley, it is to be understood that variations in the usual magnitude incident to growing conditions, fertilization, pruning, pest control, and the cultural practices are to be expected.

Having thus described and illustrated my new variety of grapevine, I claim:

1. A new and distinct variety of grapevine substantially as illustrated and described characterized by its general resemblance to the Delight variety of grapevine (unpatented), which it most nearly resembles, in bearing an oval, almost seedless green berry, but being distinguished therefrom and characterized as to novelty by bearing berries which mature at least two weeks earlier than the Delight between June 25 and July 5, and furthermore by not having the light muscat flavor that is characteristic of the Delight variety.

* * * * *

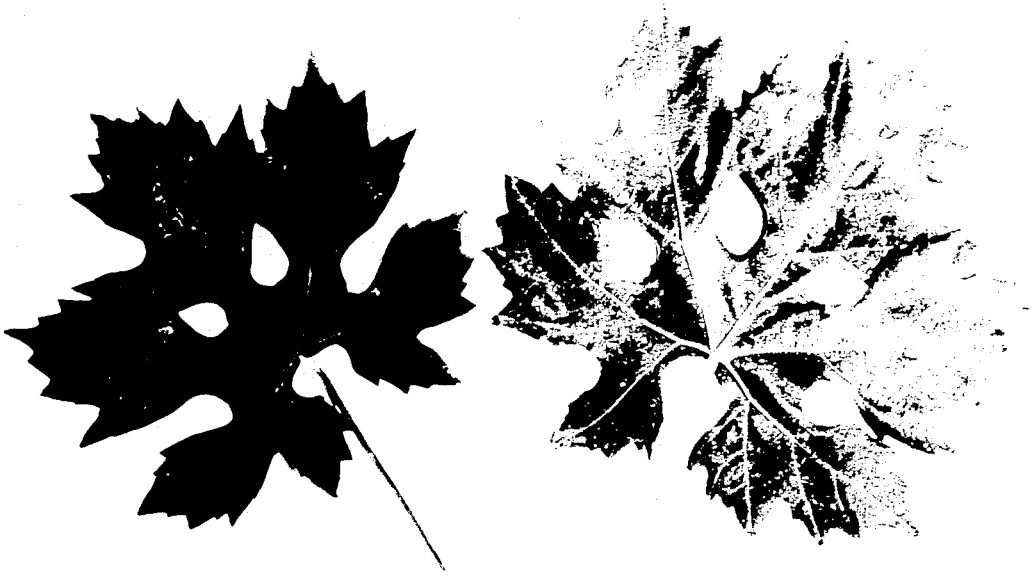
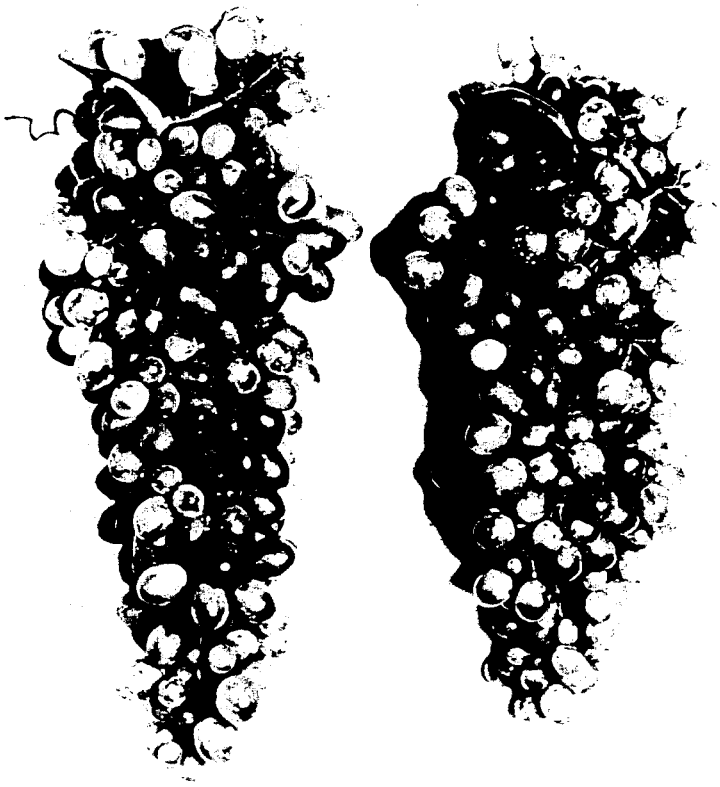

UNITED STATES PATENT AND TRADEMARK OFFICE

CERTIFICATE OF CORRECTION

PATENT NO. : PP 5,908

DATED : March 17, 1987

INVENTOR(S) : John M. Garabedian

It is certified that error appears in the above-identified patent and that said Letters Patent is hereby corrected as shown below:

Column 4, line 17, delete "resin" and substitute ---raisin---.

Signed and Sealed this

Thirtieth Day of June, 1987

*Attest:*

DONALD J. QUIGG

*Attesting Officer*

*Commissioner of Patents and Trademarks*